US009763808B2

United States Patent
Jonsson (10) Patent No.: US 9,763,808 B2
(45) Date of Patent: Sep. 19, 2017

(54) ADJUSTABLE PROSTHETIC DEVICE

(71) Applicant: OSSUR HF, Reykjavik (IS)

(72) Inventor: Grimur Jonsson, Vogar (IS)

(73) Assignee: OSSUR HF, Reyjavik (IS)

( * ) Notice: Subject to any disclaimer, the term of this patent is extended or adjusted under 35 U.S.C. 154(b) by 41 days.

(21) Appl. No.: 14/715,806

(22) Filed: May 19, 2015

(65) Prior Publication Data

US 2015/0328018 A1 Nov. 19, 2015

Related U.S. Application Data

(60) Provisional application No. 62/000,154, filed on May 19, 2014.

(51) Int. Cl.
*A61F 2/66* (2006.01)
*A61F 2/50* (2006.01)
(Continued)

(52) U.S. Cl.
CPC ............. *A61F 2/66* (2013.01); *A61F 2/50* (2013.01); *A61F 2/60* (2013.01); *A61F 2/7812* (2013.01);
(Continued)

(58) Field of Classification Search
CPC .. A61F 2/5044; A61F 2/60; A61F 2/66; A61F 2/78; A61F 2/7812;
(Continued)

(56) References Cited

U.S. PATENT DOCUMENTS

| 37,282 A | 1/1863 | Engelbrecht et al. |
| 51,593 A | 12/1865 | Jewett |

(Continued)

FOREIGN PATENT DOCUMENTS

| CA | 2 112 789 A1 | 8/1994 |
| CA | 2 114 387 A1 | 8/1994 |

(Continued)

OTHER PUBLICATIONS

Hikari, Giken. Derwent abstract of JP3170433. Sep. 15, 2011. A43B23/02.*

(Continued)

*Primary Examiner* — Thomas J Sweet
*Assistant Examiner* — Christie Bahena
(74) *Attorney, Agent, or Firm* — Workman Nydegger (57) ABSTRACT

A prosthetic device is configurable between a predetermined shape configuration and a contracted configuration. The prosthetic device includes a resilient body having the predetermined shape configuration and defining a first surface and a second surface opposed to the first surface and separated by a wall thickness. An adjustment device is connected to the resilient body, and at least one elongate element engages at least one of the first and second surfaces and has a first end received by the adjustment device such that the adjustment device is arranged to regulate tension in the at least one elongate element. Tensioning of the at least one elongate element by the adjustment device urges the resilient body to collapse or compress into the contracted configuration, wherein release of tension of the at least one elongate element allows the resilient body to revert to the predetermined shape configuration.

3 Claims, 3 Drawing Sheets

(51) Int. Cl.
 *A61F 2/78* (2006.01)
 *A61F 2/60* (2006.01)
(52) U.S. Cl.
 CPC ......... *A61F 2/78* (2013.01); *A61F 2002/5001* (2013.01); *A61F 2002/5016* (2013.01); *A61F 2002/5027* (2013.01); *A61F 2002/6614* (2013.01); *A61F 2002/7837* (2013.01)
(58) Field of Classification Search
 CPC ...... A61F 2002/5001; A61F 2002/5007; A61F 2002/5016; A61F 2002/5026; A61F 2002/5027; A61F 2002/5044; A61F 2002/5081; A61F 2002/5083; A61F 2002/607; A61F 2002/7806; A61F 2002/7856; A61F 2002/7868; A61F 2002/7881; A43B 5/00; A43B 5/0447; A43C 13/002; A43C 13/004; A43C 13/008; A43C 13/14; A43C 13/165
 See application file for complete search history.

(56) References Cited

U.S. PATENT DOCUMENTS

| | | |
|---|---|---|
| 366,494 A | 7/1887 | Marks |
| 470,431 A | 3/1892 | Marks |
| 1,066,605 A | 7/1913 | Hanger |
| 1,144,681 A | 6/1915 | Apgar |
| 1,893,853 A | 1/1933 | Tullis |
| 2,070,093 A | 2/1937 | Roe |
| 2,229,728 A | 1/1941 | Eddels |
| 2,634,424 A | 4/1953 | O'Gorman |
| 2,669,728 A | 2/1954 | Ritchie |
| 3,793,749 A | 2/1974 | Gertsch et al. |
| 3,808,644 A | 5/1974 | Schoch |
| 3,889,664 A | 6/1975 | Heuser et al. |
| 3,926,182 A | 12/1975 | Stabholz |
| 4,128,903 A | 12/1978 | Marsh et al. |
| 4,161,042 A | 7/1979 | Cottingham et al. |
| 4,261,081 A | 4/1981 | Lott |
| 4,268,922 A | 5/1981 | Marsh et al. |
| 4,300,245 A | 11/1981 | Saunders |
| 4,433,456 A | 2/1984 | Baggio |
| 4,459,709 A | 7/1984 | Leal et al. |
| 4,551,932 A | 11/1985 | Schoch |
| 4,555,830 A | 12/1985 | Petrini et al. |
| 4,574,500 A | 3/1986 | Aldinio et al. |
| 4,616,524 A | 10/1986 | Bidoia |
| 4,619,657 A | 10/1986 | Keates et al. |
| 4,620,378 A * | 11/1986 | Sartor ................. A43B 5/0449 36/117.8 |
| 4,631,839 A | 12/1986 | Bonetti et al. |
| 4,631,840 A | 12/1986 | Gamm |
| 4,633,599 A | 1/1987 | Morell et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,741,115 A | 5/1988 | Pozzobon |
| 4,748,726 A | 6/1988 | Schoch |
| 4,760,653 A | 8/1988 | Baggio |
| 4,783,293 A | 11/1988 | Wellershaus et al. |
| 4,799,297 A | 1/1989 | Baggio et al. |
| 4,802,291 A | 2/1989 | Sartor |
| 4,811,503 A | 3/1989 | Iwama |
| 4,841,649 A | 6/1989 | Baggio et al. |
| 4,842,608 A | 6/1989 | Marx et al. |
| 4,872,879 A | 10/1989 | Shamp |
| 4,884,760 A | 12/1989 | Baggio et al. |
| 4,921,502 A | 5/1990 | Shamp |
| 4,938,775 A | 7/1990 | Morgan |
| 4,961,544 A | 10/1990 | Bidoia |
| 4,988,360 A | 1/1991 | Shamp |
| 5,042,177 A | 8/1991 | Schoch |
| 5,062,225 A | 11/1991 | Gorza |
| 5,065,481 A | 11/1991 | Walkhoff |
| 5,092,321 A | 3/1992 | Spademan |
| 5,108,456 A | 4/1992 | Coonan, III |
| 5,117,567 A | 6/1992 | Berger |
| 5,133,777 A | 7/1992 | Arbogast et al. |
| 5,152,038 A | 10/1992 | Schoch |
| 5,157,813 A | 10/1992 | Carroll |
| 5,177,882 A | 1/1993 | Berger |
| 5,181,331 A | 1/1993 | Berger |
| 5,183,036 A | 2/1993 | Spademan |
| 5,201,773 A | 4/1993 | Carideo, Jr. |
| 5,201,775 A | 4/1993 | Arbogast et al. |
| 5,246,464 A | 9/1993 | Sabolich |
| 5,249,377 A | 10/1993 | Walkhoff |
| 5,312,669 A | 5/1994 | Bedard |
| 5,319,868 A | 6/1994 | Hallenbeck |
| 5,325,613 A | 7/1994 | Sussmann |
| 5,327,662 A | 7/1994 | Hallenbeck |
| 5,365,947 A | 11/1994 | Bonutti |
| 5,424,782 A | 6/1995 | Aoki |
| 5,433,648 A | 7/1995 | Frydman |
| 5,437,619 A | 8/1995 | Malewicz et al. |
| 5,477,593 A | 12/1995 | Leick |
| 5,502,902 A | 4/1996 | Sussmann |
| 5,503,543 A | 4/1996 | Laghi |
| 5,529,575 A | 6/1996 | Klotz |
| 5,545,231 A | 8/1996 | Houser |
| 5,571,209 A | 11/1996 | Brown, Sr. |
| 5,599,288 A | 2/1997 | Shirley et al. |
| 5,638,588 A | 6/1997 | Jungkind |
| 5,647,104 A | 7/1997 | James |
| 5,653,766 A | 8/1997 | Naser |
| 5,669,116 A | 9/1997 | Jungkind |
| 5,685,830 A | 11/1997 | Bonutti |
| 5,718,925 A | 2/1998 | Kristinsson et al. |
| 5,728,165 A | 3/1998 | Brown, Sr. |
| 5,732,483 A | 3/1998 | Cagliari |
| 5,737,854 A | 4/1998 | Sussmann |
| 5,800,569 A | 9/1998 | Phillips |
| 5,819,378 A | 10/1998 | Doyle |
| 5,824,111 A | 10/1998 | Schall et al. |
| 5,848,979 A | 12/1998 | Bonutti et al. |
| 5,885,509 A | 3/1999 | Kristinsson |
| 5,888,215 A | 3/1999 | Roos et al. |
| 5,888,217 A | 3/1999 | Slemker |
| 5,891,061 A | 4/1999 | Kaiser |
| 5,934,599 A | 8/1999 | Hammerslag |
| 5,993,488 A | 11/1999 | Phillips |
| 6,136,039 A | 10/2000 | Kristinsson et al. |
| 6,159,248 A | 12/2000 | Gramnas |
| 6,202,953 B1 | 3/2001 | Hammerslag |
| 6,206,932 B1 | 3/2001 | Johnson |
| 6,256,798 B1 | 7/2001 | Egolf et al. |
| 6,267,390 B1 | 7/2001 | Maravetz et al. |
| 6,280,479 B1 | 8/2001 | Phillips |
| 6,289,558 B1 | 9/2001 | Hammerslag |
| 6,368,357 B1 | 4/2002 | Schon et al. |
| 6,413,232 B1 | 7/2002 | Townsend et al. |
| 6,416,074 B1 | 7/2002 | Maravetz et al. |
| 6,497,028 B1 | 12/2002 | Rothschild et al. |
| 6,500,210 B1 | 12/2002 | Sabolich et al. |
| 6,502,577 B1 | 1/2003 | Bonutti |
| 6,503,213 B2 | 1/2003 | Bonutti |
| 6,557,177 B2 | 5/2003 | Hochmuth |
| 6,626,952 B2 | 9/2003 | Janusson et al. |
| 6,643,954 B2 * | 11/2003 | Voswinkel ............. A43B 11/00 36/138 |
| 6,689,080 B2 | 2/2004 | Castillo |
| 6,711,787 B2 | 3/2004 | Jungkind et al. |
| 6,769,155 B2 | 8/2004 | Hess et al. |
| 6,770,047 B2 | 8/2004 | Bonutti |
| 6,793,682 B1 | 9/2004 | Mantelmacher |
| 6,827,653 B2 | 12/2004 | Be |
| 6,921,377 B2 | 7/2005 | Bonutti |
| 6,942,703 B2 | 9/2005 | Carstens |

(56) References Cited

U.S. PATENT DOCUMENTS

| | | | |
|---|---|---|---|
| 6,991,657 | B1 | 1/2006 | Price, Jr. |
| D519,637 | S | 4/2006 | Nordt et al. |
| D520,141 | S | 5/2006 | Nordt et al. |
| D521,644 | S | 5/2006 | Nordt et al. |
| 7,094,212 | B2 | 8/2006 | Karason et al. |
| 7,105,122 | B2 | 9/2006 | Karason |
| 7,118,602 | B2 | 10/2006 | Bjarnason |
| 7,128,724 | B2 | 10/2006 | Marsh |
| 7,134,224 | B2 | 11/2006 | Elkington et al. |
| 7,172,714 | B2 | 2/2007 | Jacobson |
| 7,198,610 | B2 | 4/2007 | Ingimundarson et al. |
| 7,207,126 | B2 | 4/2007 | Gantier |
| 7,235,059 | B2 | 6/2007 | Mason et al. |
| 7,240,414 | B2 | 7/2007 | Taylor, Sr. |
| 7,281,341 | B2 | 10/2007 | Reagan et al. |
| 7,288,116 | B2 | 10/2007 | Ikeda |
| 7,306,573 | B2 | 12/2007 | Bonutti |
| 7,331,126 | B2 | 2/2008 | Johnson |
| 7,344,567 | B2 | 3/2008 | Slemker |
| 7,402,147 | B1 | 7/2008 | Allen |
| 7,402,265 | B2 | 7/2008 | Jacobson |
| 7,404,804 | B2 | 7/2008 | Bonutti |
| 7,416,565 | B1 | 8/2008 | Al-Turaikl |
| 7,438,698 | B2 | 10/2008 | Daiju |
| 7,438,843 | B2 | 10/2008 | Asgeirsson |
| 7,488,349 | B2 | 2/2009 | Einarsson |
| 7,513,018 | B2 | 4/2009 | Koenig et al. |
| 7,591,050 | B2 | 9/2009 | Hammerslag |
| 7,600,660 | B2 | 10/2009 | Kasper et al. |
| 7,617,573 | B2 | 11/2009 | Chen |
| 7,618,386 | B2 | 11/2009 | Nordt, III et al. |
| 7,618,389 | B2 | 11/2009 | Nordt, III et al. |
| 7,640,680 | B1 * | 1/2010 | Castro .................... A43B 7/00 36/140 |
| 7,670,306 | B2 | 3/2010 | Nordt, III et al. |
| 7,699,797 | B2 | 4/2010 | Nordt, III et al. |
| 7,704,219 | B2 | 4/2010 | Nordt, III et al. |
| 7,727,284 | B2 | 6/2010 | Warila |
| 7,771,488 | B2 | 8/2010 | Asgeirsson et al. |
| 7,806,842 | B2 | 10/2010 | Stevenson et al. |
| 7,818,899 | B2 * | 10/2010 | Dinndorf ............ A43B 3/0031 36/4 |
| 7,857,776 | B2 | 12/2010 | Frisbie |
| 7,862,621 | B2 | 1/2011 | Kloos et al. |
| 7,867,286 | B2 | 1/2011 | Einarsson |
| 7,878,998 | B2 | 2/2011 | Nordt, III et al. |
| 7,887,500 | B2 | 2/2011 | Nordt, III et al. |
| 7,922,680 | B2 | 4/2011 | Nordt, III et al. |
| 7,950,112 | B2 | 5/2011 | Hammerslag et al. |
| 7,954,204 | B2 | 6/2011 | Hammerslag et al. |
| 7,985,192 | B2 | 7/2011 | Sheehan et al. |
| 7,993,296 | B2 | 8/2011 | Nordt, III et al. |
| 8,002,724 | B2 | 8/2011 | Hu et al. |
| 8,007,544 | B2 | 8/2011 | Jonsson et al. |
| 8,038,635 | B2 | 10/2011 | Dellanno |
| 8,038,637 | B2 | 10/2011 | Bonutti |
| 8,088,320 | B1 | 1/2012 | Bedard |
| 8,091,182 | B2 | 1/2012 | Hammerslag et al. |
| 8,097,043 | B2 | 1/2012 | Egilsson |
| 8,123,818 | B2 | 2/2012 | Bjarnason et al. |
| 8,303,527 | B2 | 11/2012 | Joseph |
| 8,308,815 | B2 | 11/2012 | McCarthy |
| 8,323,353 | B1 | 12/2012 | Alley et al. |
| 8,414,658 | B2 | 4/2013 | Johnson et al. |
| 2002/0077703 | A1 * | 6/2002 | Johnson ................ A61F 2/5046 623/27 |
| 2002/0095750 | A1 | 7/2002 | Hammerslag |
| 2002/0099450 | A1 | 7/2002 | Dean, Jr. et al. |
| 2003/0093882 | A1 | 5/2003 | Gorza et al. |
| 2003/0181990 | A1 | 9/2003 | Phillips |
| 2003/0204938 | A1 | 11/2003 | Hammerslag |
| 2005/0081339 | A1 | 4/2005 | Sakabayashi |
| 2005/0160627 | A1 | 7/2005 | Dalgaard et al. |
| 2005/0247813 | A1 | 11/2005 | Kovacevich et al. |
| 2005/0273025 | A1 | 12/2005 | Houser |
| 2005/0284003 | A1 | 12/2005 | Dalgaard et al. |
| 2006/0009860 | A1 | 1/2006 | Price, Jr. |
| 2006/0015980 | A1 | 1/2006 | Nordt, III et al. |
| 2006/0015988 | A1 | 1/2006 | Philpott et al. |
| 2006/0020237 | A1 | 1/2006 | Nordt, III et al. |
| 2006/0026732 | A1 | 2/2006 | Nordt, III et al. |
| 2006/0026733 | A1 | 2/2006 | Nordt, III et al. |
| 2006/0026736 | A1 | 2/2006 | Nordt, III et al. |
| 2006/0030802 | A1 | 2/2006 | Nordt, III et al. |
| 2006/0030803 | A1 | 2/2006 | Nordt, III et al. |
| 2006/0030804 | A1 | 2/2006 | Nordt, III et al. |
| 2006/0030805 | A1 | 2/2006 | Nordt, III et al. |
| 2006/0030806 | A1 | 2/2006 | Nordt, III et al. |
| 2006/0070164 | A1 | 4/2006 | Nordt, III et al. |
| 2006/0070165 | A1 | 4/2006 | Nordt, III et al. |
| 2006/0135900 | A1 | 6/2006 | Ingimundarson et al. |
| 2006/0156517 | A1 | 7/2006 | Hammerslag et al. |
| 2006/0174516 | A1 | 8/2006 | Peruzzo |
| 2006/0185357 | A1 | 8/2006 | Kovacevich et al. |
| 2006/0202077 | A1 | 9/2006 | Kovacevich et al. |
| 2006/0202078 | A1 | 9/2006 | Kovacevich et al. |
| 2007/0004993 | A1 | 1/2007 | Coppens et al. |
| 2007/0039085 | A1 | 2/2007 | Kovacevich et al. |
| 2007/0078523 | A1 | 4/2007 | Kholwadwala et al. |
| 2007/0152379 | A1 | 7/2007 | Jacobson |
| 2007/0169378 | A1 | 7/2007 | Sodeberg et al. |
| 2008/0034459 | A1 | 2/2008 | Nordt, III et al. |
| 2008/0039757 | A1 | 2/2008 | Nordt, III et al. |
| 2008/0039764 | A1 | 2/2008 | Nordt, III et al. |
| 2008/0039765 | A1 | 2/2008 | Nordt, III et al. |
| 2008/0039767 | A1 | 2/2008 | Nordt, III et al. |
| 2008/0060167 | A1 | 3/2008 | Hammerslag et al. |
| 2008/0060168 | A1 | 3/2008 | Hammerslag et al. |
| 2008/0066272 | A1 | 3/2008 | Hammerslag et al. |
| 2008/0066345 | A1 | 3/2008 | Hammerslag et al. |
| 2008/0066346 | A1 | 3/2008 | Hammerslag et al. |
| 2008/0083135 | A1 | 4/2008 | Hammerslag et al. |
| 2008/0091132 | A1 | 4/2008 | Bonutti |
| 2008/0269914 | A1 | 10/2008 | Coppens et al. |
| 2008/0319362 | A1 | 12/2008 | Joseph |
| 2009/0030353 | A1 | 1/2009 | Bonutti et al. |
| 2009/0076625 | A1 | 3/2009 | Groves et al. |
| 2009/0090026 | A1 | 4/2009 | Mosher |
| 2009/0105844 | A1 | 4/2009 | Ortiz |
| 2009/0287128 | A1 | 11/2009 | Ingimundarson et al. |
| 2010/0030344 | A1 | 2/2010 | Hansen et al. |
| 2010/0036300 | A1 | 2/2010 | Sheehan et al. |
| 2010/0036505 | A1 | 2/2010 | Hassler |
| 2010/0082116 | A1 | 4/2010 | Johnson et al. |
| 2010/0121464 | A1 | 5/2010 | Mantelmacher |
| 2010/0139057 | A1 | 6/2010 | Soderberg et al. |
| 2010/0191348 | A1 | 7/2010 | Kettwig et al. |
| 2010/0268139 | A1 | 10/2010 | Garth |
| 2010/0274364 | A1 | 10/2010 | Pacanowsky et al. |
| 2010/0299959 | A1 | 12/2010 | Hammerslag et al. |
| 2011/0035027 | A1 | 2/2011 | McCarthy |
| 2011/0046528 | A1 | 2/2011 | Stevenson et al. |
| 2011/0071647 | A1 | 3/2011 | Mahon |
| 2011/0082402 | A1 | 4/2011 | Oddou et al. |
| 2011/0098618 | A1 | 4/2011 | Fleming |
| 2011/0114635 | A1 | 5/2011 | Sheehan |
| 2011/0144554 | A1 | 6/2011 | Weaver, II et al. |
| 2011/0178448 | A1 | 7/2011 | Einarsson |
| 2011/0184326 | A1 | 7/2011 | Ingimundarson et al. |
| 2011/0197362 | A1 | 8/2011 | Chella et al. |
| 2011/0232837 | A9 | 9/2011 | Ottleben |
| 2011/0266384 | A1 * | 11/2011 | Goodman ............ A43C 11/165 242/396.4 |
| 2011/0320010 | A1 | 12/2011 | Vo |
| 2012/0010547 | A1 | 1/2012 | Hinds |
| 2012/0022667 | A1 | 1/2012 | Accinni et al. |
| 2012/0029404 | A1 | 2/2012 | Weaver, II et al. |
| 2012/0041567 | A1 | 2/2012 | Cornell |
| 2012/0095570 | A1 | 4/2012 | Marquette |
| 2012/0101417 | A1 | 4/2012 | Joseph |
| 2012/0101597 | A1 | 4/2012 | Bache |
| 2012/0143077 | A1 | 6/2012 | Sanders et al. |
| 2012/0253475 | A1 | 10/2012 | Kelley et al. |
| 2012/0271210 | A1 | 10/2012 | Galea et al. |

(56) References Cited

U.S. PATENT DOCUMENTS

| | | |
|---|---|---|
| 2012/0271433 A1 | 10/2012 | Galea et al. |
| 2012/0283846 A1 | 11/2012 | Janssen et al. |
| 2013/0123940 A1 | 5/2013 | Hurley et al. |
| 2013/0218297 A1* | 8/2013 | Nordman, Jr. ............ A61F 2/66 623/53 |
| 2013/0245785 A1 | 9/2013 | Accini et al. |
| 2015/0018973 A1* | 1/2015 | Rana ..................... A61F 2/66 623/29 |
| 2015/0051711 A1 | 2/2015 | Egilsson et al. |

FOREIGN PATENT DOCUMENTS

| | | |
|---|---|---|
| CH | 577 282 A5 | 7/1976 |
| CH | 612 076 A5 | 7/1979 |
| CH | 624 001 A5 | 7/1981 |
| DE | 2 341 658 A1 | 3/1974 |
| DE | 38 22 113 A1 | 1/1990 |
| DE | 93 15 776.2 U1 | 2/1995 |
| DE | 295 03 552.8 U1 | 4/1995 |
| DE | 199 45 045 A1 | 3/2001 |
| DE | 100 57 286 A1 | 5/2002 |
| EP | 0 201 051 A1 | 11/1986 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0 589 232 B1 | 11/1995 |
| EP | 0 693 260 B1 | 9/1998 |
| EP | 0 651 954 B1 | 2/1999 |
| EP | 1 236 412 A1 | 9/2002 |
| EP | 1 433 447 A2 | 6/2004 |
| FR | 2 177 294 A6 | 11/1973 |
| FR | 2 399 811 A1 | 3/1979 |
| GB | 127 451 A | 6/1919 |
| JP | 3031760 U | 12/1996 |
| JP | 2004-016732 A | 1/2004 |
| JP | 2004-041666 A | 2/2004 |
| WO | 91/16019 A1 | 10/1991 |
| WO | 95/03720 A2 | 2/1995 |
| WO | 97/03581 A1 | 2/1997 |
| WO | 98/12994 A1 | 4/1998 |
| WO | 00/53045 A1 | 9/2000 |
| WO | 2004/110197 A2 | 12/2004 |
| WO | 2007/016983 A1 | 2/2007 |
| WO | 2007/035875 A2 | 3/2007 |
| WO | 2008/116025 A2 | 9/2008 |
| WO | 2009/093020 A2 | 7/2009 |
| WO | 2012/021823 A1 | 2/2012 |
| WO | 2013/071308 A1 | 5/2013 |

OTHER PUBLICATIONS

"Rollerblade TFS Skate Laces AERO", http://www.inlinewarehouse.com/viewlarge.html?PCODE=TFS, retrieved on Jan. 7, 2010, 1 page.

"Rollerblade TFS Skate Laces MICRO", http://www.inlinewarehouse.com/viewlarge.html?PCODE=MILC, retrieved on Jan. 7, 2010, 1 page.

International Search Report from International Application No. PCT/US2011/057043, Jan. 27, 2012.

Otto Bock Quality for Life: Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.

International Search Report from International Application No. PCT/US2013/048675, Oct. 9, 2013.

Manual: "Socket Evaluation System with the Rapid Adjustment Pylon, Owner's Manual and Operating Insturctions", [retrieved from the internet on May 22, 2014], <URL:http://www.fillauer.com>; 4 pages.

International Search Report and Written Opinion from Corresponding International PCT Application No. PCT/US2015/031468, Jul. 28, 2015.

* cited by examiner

ADJUSTABLE PROSTHETIC DEVICE

FIELD OF THE DISCLOSURE

The present disclosure relates to the field of prosthetics, and more particularly, to an adjustable prosthetic device for an artificial or residual limb.

BACKGROUND

Amputees commonly use prosthetic devices to improve their mobility and associated quality of life. Various types of prosthetic devices are available for amputees, including prosthetic limbs such as artificial feet and hands. Such artificial limbs are secured to a wearer to restore the impaired or lost functionality of the amputee's residual limbs. These prosthetic devices serve as replacement limbs so the amputee can maintain a normal quality of life. The ability to achieve full use of a prosthetic limb is an important factor in both the physical and mental rehabilitation of an amputee.

Conventional prosthetic limbs are sometimes enclosed in a cosmesis or cover to improve their aesthetic appeal. The cosmesis for an artificial foot serves as a cosmetic casing that provides the appearance of a natural looking foot for the lower limb amputee. The artificial limb can be provided with an authentic look by incorporating natural skin color and texture to the cosmesis for mimicking that of the amputee. This provides a natural appearance so it is not noticeable that an amputee is wearing a prosthesis.

The cosmesis can protect the prosthesis and any of its components from wear and tear caused by the environment, increasing the life of the prosthesis. Using a cosmesis can prevent dirt and debris from interfering with the mechanical components of the prosthetic limb. Further, the cosmesis may be available as either a part of a prosthesis, or as a separate attachment for a prosthesis.

Using a foot cosmesis can help an amputee achieve a normal appearance when out in public. Typical foot cosmetic covers, however, can disadvantageously be limited in the flexibility and versatility they provide in allowing the amputee to don different conventional footwear, such as sneakers or boots. The repeated frictional contact between the footwear and the cosmesis during donning and doffing can cause wear on the cosmesis damaging it. This not only results in inconvenient frequent replacement of the cosmesis, but it also further adds to the cost for the amputee to constantly fix or replace the damaged cosmesis. There is a substantial need for a cosmesis for an artificial foot capable of providing easy and quick donning and doffing of footwear.

Most common cosmetic covers are form-fitted over an artificial limb, or use adhesive or suction to bond the cover to the limb. Such covers can be costly to provide a desired fit. These covers are generally only made to fit a specific artificial or residual limb. For instance, if the amputee replaces a particular artificial limb, then the cover will also likely need to be replaced with the artificial limb.

Conventional covers may be molded from synthetic material, such as foam rubber. These covers are often bonded to an artificial limb by an adhesive inserted into the hollow space inside the cover. Adhesives have disadvantages. If the artificial limb requires repair or readjustment, the adhesion surface of the cover should be cut open to gain access to the artificial limb. There is a greater possibility of damaging the artificial limb if the cover requires replacement.

Separating an adhesively bonded cover from an artificial limb can be difficult and time consuming. Even when an adhesively bonded cover is successfully removed from an artificial limb, it's difficult to reapply additional adhesive to the cover for reattachment to the limb. This may diminish the cover's cosmetic effect. There is a clear need for a non-permanent way of securing a cosmesis to an artificial limb.

Other cosmetic covers commonly utilize a snap-on or press-fit connection for securing to an artificial limb. Although such a connection may seem easy for a user to snap the cover into place, it provides no way to make donning or doffing a shoe any easier since the cover remains the same size when attached. A snap-on connection provides no way for a user to adjustably tighten or loosen the cover onto the artificial limb as desired.

Form-fitting cosmetic covers are not universally accepted onto all artificial limbs. Properly fitting and securing a prosthetic device to an amputee is often difficult because artificial limbs and residual limbs can be various shapes and sizes—and various size covers may be needed. This lack of versatility prohibits such covers from fitting onto numerous existing prosthetic limbs.

Many conventional covers have a tendency to become loose while being worn throughout the day. Without sufficiently securing a cosmesis to an artificial foot, the frictional contact between the artificial foot and the cosmesis can cause wear on the cosmesis over time, especially at high stress contact points. This can cause the amputee having to frequently replace or repair the damaged cosmesis increasing the cost to the amputee. There is a substantial need for a cosmesis that can easily and quickly be selectively adjusted for proper fitting, such as for allowing a user to tighten the cosmesis as needed.

SUMMARY

According to an embodiment of the disclosure, a prosthetic device includes a resilient body having a predetermined shape configuration. The resilient body defines a first surface and a second surface opposed to the first surface and separated by a wall thickness. An adjustment device connects to the resilient body, and at least one elongate element engages at least one of the first and second surfaces. The at least one elongate element has a first end received by the adjustment device such that the adjustment device is arranged to regulate tension in the at least one elongate element.

The prosthetic device is arranged for being adjusted into different shape configurations to accommodate different needs, such as for donning a foot cosmesis into a shoe or providing addition sealing means in a brim attachment for a prosthetic socket. Tensioning of the at least one elongate element by the adjustment device urges the resilient body to collapse or compress into a contracted configuration. Release of tension of the at least one elongate element allows the resilient body to revert to the predetermined shape configuration.

At least one guide may be provided on one of the first or second surfaces through which the at least one elongate element extends. The at least one guide may be on the first surface which may be defined as an interior surface of the resilient body. The interior surface delimits a cavity of the resilient body. The at least one guide may be a channel located only along an upper portion of the resilient body. A lower portion of the resilient body may be not compressed or collapsed upon tensioning of the elongate element, and generally locally retain the predetermined shape configuration. A segment of the at least one elongate element may be anchored to the at least one guide such that tensioning of the at least one elongate element pulls from the segment and toward the adjustment device.

Additional means may be connected to the at least one elongate element to facilitate return of the resilient body to the predetermined shape configuration. A spring, bar or other spring-type element may be connected or attached to the at least one elongate element to assist in releasing tension in the at least one elongate element. The tension may be released by the adjustment device by unlocking unidirectional tensioning of the adjustment device. The adjustment device may be a dial tensioning device arranged to incrementally wind and tension the at least one elongate element, a linear ratchet or other suitable devices allowing for locking unidirectional and release of an elongate element.

The resilient body defines an opening through the thickness of which the at least one elongate element extends between the first and second surfaces. The at least one elongate element may extend through a network of guides located along the first surface and arranged in a pattern to urge collapse of the resilient body into the contracted configuration. The network of guides may be arranged so the lower portion remains in the predetermined shape configuration, such as being without any guides.

When the prosthetic device is a foot cosmesis, the resilient body is arranged to receive a prosthetic foot at least in the lower portion. The network of guides may be located in the upper portion such that the contracted configuration of the resilient body results in collapsing of the upper portion over the lower portion and the prosthetic foot.

In another embodiment, the prosthetic device is a brim attachment for attaching to a proximal end of a hard prosthetic socket arranged for being worn by limb amputee. At least one guide is on the brim attachment and an adjustment device and elongate element are provided for urging the brim attachment toward the residual limb upon tensioning of the elongate element. A network of guides may be provided on the brim attachment and the hard socket itself to better tighten the brim attachment against the residual limb.

A frictional feature may be disposed on one of the first and second surfaces for maintaining the shape of the resilient body in the contracted configuration. The frictional feature may have greater frictional properties than the one of the first and second surfaces upon which it is located. The frictional feature may be at a fold portion of the resilient body. The frictional feature may be only on the one of the first and second surfaces at an upper portion thereof.

The prosthetic device may be employed as part of a prosthesis system. A lower leg prosthesis system includes a prosthetic foot, a foot cosmesis having a resilient body with an inner cavity arranged for receiving the prosthetic foot. The resilient body has a predetermined shape configuration, and the resilient body defines an inner surface delimiting the inner cavity and an outer surface opposed to the inner surface and separated by a wall thickness. An adjustment device connects to the resilient body, and at least one elongate element engages at least one of the inner and outer surfaces. The at least one elongate element has a first end received by the adjustment device such that the adjustment device is arranged to regulate tension in the at least one elongate element. Tensioning of the at least one elongate element by the adjustment device urges the resilient body to collapse or compress into a contracted configuration. Release of tension of the at least one elongate element allows the resilient body to revert to the predetermined shape configuration.

The at least one elongate element may extend through at least one guide along the one of the inner and outer surfaces to urge collapse of the resilient body into the contracted configuration. The resilient body defines dorsal and plantar portions. The foot cosmesis may be arranged for placement of the prosthetic foot in the lower portion. The at least one guide is in the dorsal portion such that the contracted configuration of the resilient body results in collapsing of the dorsal portion over the plantar portion and the prosthetic foot.

A method for modifying the shape of a prosthetic device comprises the steps of tensioning of the at least one elongate element by the adjustment device to urge the resilient body to collapse or compress into a contracted configuration, and releasing tension of the at least one elongate element to allow the resilient body to revert to the predetermined shape configuration. The tension in the at least one elongate element may be maintained by incremental locking as the adjustment device is regulated.

According to the embodiments, an adjustable prosthetic device is provided that enables easy and quick donning and doffing of a prosthetic device, such as a prosthetic foot and its placement in a shoe, or assuring sealing of a brim attachment. The solutions provided by the embodiments offer a non-permanent way of securing a cosmesis to an artificial limb, and enable versatility in size by which they are secured due to incremental tensioning and contraction of the prosthetic device. The adjustment device provides quick and easy selective adjustment for proper fitting, such as for allowing a user to tighten the cosmesis or brim attachment as needed.

BRIEF DESCRIPTION OF THE DRAWINGS

The numerous other advantages, features and functions of embodiments of an adjustable prosthetic device and related concepts will become readily apparent and better understood in view of the following description and accompanying drawings. The following description is not intended to limit the scope of the prosthetic device, but instead merely provides exemplary embodiments for ease of understanding.

The drawing figures are not necessarily drawn to scale, but instead are drawn to provide a better understanding of the components thereof, and are not intended to be limiting in scope, but to provide exemplary illustrations. The figures illustrate exemplary configurations of an adjustable prosthetic device, and in no way limit the structures or configurations of the adjustable prosthetic device according to the present disclosure.

DETAILED DESCRIPTION OF VARIOUS EMBODIMENTS

A. Overview

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, there is no intention to limit the disclosure to the embodiments disclosed, but on the contrary, the intention is to cover all modifications, alternative constructions, combinations, and equivalents falling within the spirit and scope of the disclosure.

It will be understood that, unless a term is defined to possess a described meaning, there is no intent to limit the meaning of such term, either expressly or indirectly, beyond its plain or ordinary meaning.

Any element in a claim that does not explicitly state "means for" performing a specified function, or "step for" performing a function is not to be interpreted as a "means" or "step" clause as specified in 35 U.S.C. §112, paragraph 6.

B. Definitions

For ease of understanding the disclosed embodiments of an adjustable prosthetic device, the anterior and posterior portions of the prosthetic device may be described independently. Anterior and posterior portions of the prosthetic device function together to support and stabilize anatomical portions of the wearer of the device.

As used herein, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Lastly, the term "anterior" has its ordinary meaning and refers to a location ahead of or to the front of another location.

The terms "rigid" and "flexible" and "resilient" may be used herein to distinguish characteristics of portions of certain features of the prosthetic device. The term "rigid" should denote that an element of the device is generally devoid of flexibility. Within the context of members that are "rigid," it should indicate that they do not lose their overall shape when force is applied, and they may break if bent with sufficient force. The term "flexible" should denote that features are capable of repeated bending such that the features may be bent into retained shapes or the features do not retain a general shape, but continuously deform when force is applied. The term "resilient" is similarly intended to denote that features can bend or being deformed, but can also return to their original shape.

C. Various Embodiments of the Adjustable Cover

Figure 1:
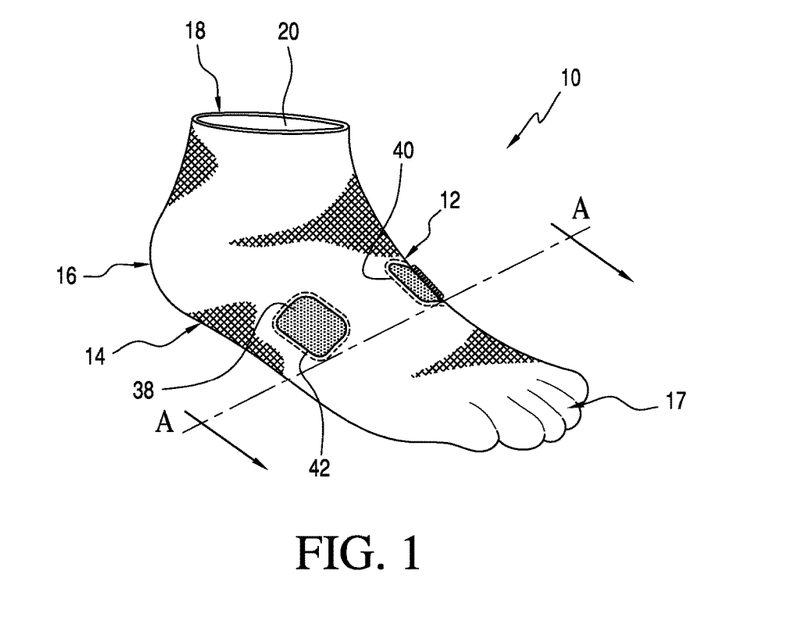
FIG. 1 is a perspective view of a foot cosmesis according to an embodiment of the invention in an expanded configuration.
Figure 2:
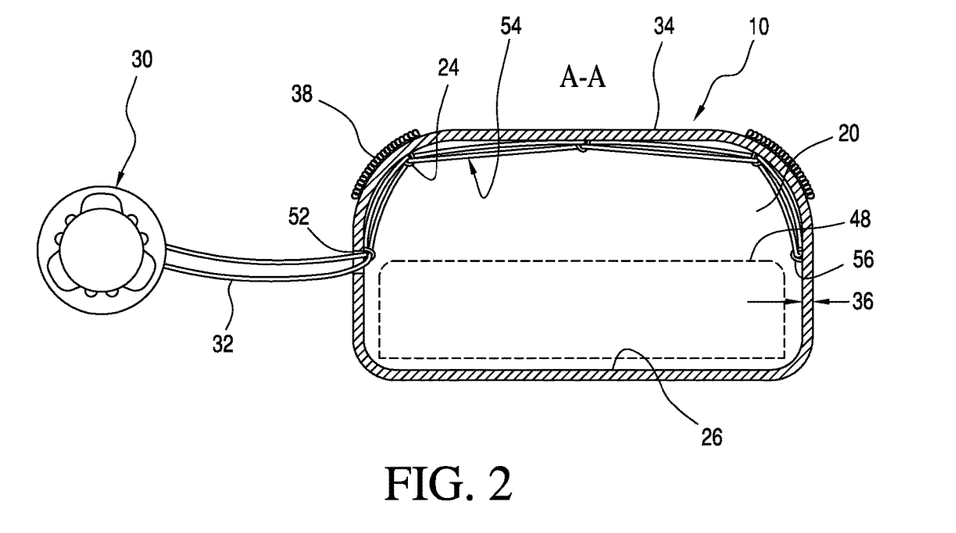
FIG. 2 is a cross-sectional view of the foot cosmesis of FIG. 1 along the line A-A.

According to an embodiment of the adjustable prosthetic device, as illustrated in FIGS. 1 and 2, a foot cosmesis or cover 10 is configured for attachment to a prosthetic foot 48 and is arranged in a predetermined shape configuration. The foot cosmesis or cover 10 may be considered a resilient body. Although a foot cosmesis is discussed in detail herein, it should be appreciated that the same or similar features of the foot cosmesis may apply to other types of cosmetic covers, brim attachments, sealing devices and other components configured for attachment to other types of artificial limbs, such as a hand cosmesis configured for attachment to a prosthetic hand. It should be appreciated that such covers as described may also be adapted for attachment to a residual limb.

Using the foot cosmesis 10 advantageously provides a way for an amputee to improve the aesthetic appearance of a prosthetic foot. The foot cosmesis 10 is generally shaped, sized and/or configured to imitate the appearance of a natural human foot. Certain covers also preferably include appendages to appear more realistic. A foot cosmesis may include toes, while a hand cosmesis may include fingers. The cosmesis may be used on a prosthetic device which may have discrete appendages already formed on it.

The cosmesis may have the color and texture of the amputee's natural skin so that the cosmesis looks like a normal limb. The foot cosmesis 10 may have a length and width substantially the same as that of a natural human foot, and is preferably sized as a natural human foot of the amputee for whom the cosmesis is intended for. The cosmesis 10 is shaped to resemble a natural foot, and includes at least a dorsal region 12, a plantar region 14, a heel or posterior region 16, a toe or anterior region 17, and an ankle region 18. The toe region 17 may be provided with slits formed between each toe for mimicking a more life-like appearance.

The cosmesis 10 further includes an inner cavity 20 delimited by an inner surface 26 and shaped, sized and/or configured to receive a prosthetic foot 48 capable of attaching to a socket of a lower limb amputee to form part of a lower leg prosthesis. Use of the cosmesis may also advantageously protect the prosthesis and any of its components from the environment, and increase the functional lifespan of the prosthesis. Exemplary materials and constructions for the footplate 48 are described in U.S. Pat. No. 7,771,488, granted Aug. 10, 2010, U.S. Pat. No. 6,280,479, granted Aug. 28, 2001, U.S. Pat. No. 5,993,488, granted Nov. 30, 1999, and U.S. Pat. No. 5,800,569, granted Sep. 1, 1998, all of which are herein incorporated by reference.

The cosmesis is preferably fabricated from a flexible and resilient material capable of providing an auxiliary cushioning support. The cosmesis 10 may comprise such resilient materials as natural or synthetic rubber, urethane foam, plastics, or other similar materials. It should be appreciated that the flexible material can accommodate repetitive movement at its joint portions, i.e. at the toe or ankle portion of the foot cover, to avoid creating excessive wrinkling or wear and tear at those locations.

It can be difficult and time consuming for an amputee to don footwear to a cosmesis secured on a prosthetic foot. It is likewise difficult to doff such footwear from the cosmesis. The frictional wear and tear endured by the cosmesis during donning and doffing of footwear can cause the cosmesis to be torn. The cosmesis 10 provides a safe way of allowing quick and easy insertion of the cosmesis and its attached prosthetic foot into footwear. Further, the cosmesis 10 provides a safe way to quickly and easily remove the cosmesis and its attached prosthetic foot from the footwear.

An adjustment device 30 may preferably be mounted to the cosmesis 10 or on an area stably secured to the cosmesis.

It should be appreciated that the adjustment device 30 is on an area easily accessible to the user, especially during use when footwear is being donned or doffed. It may be desired to place the adjustment device 30 at a location on or near the outer periphery of the ankle portion 18. A preferred placement of the adjustment device 30 would allow the user to quickly access it on the fly. The arrangement of the adjustment device preferably allows the user to access it through clothing The adjustment device 30 includes one or more elongate elements 32 and is arranged to regulate the length of a segment of the elongate element 32 extending from the adjustment device 30. The at least one elongate element 32 may comprise a pair of segments arranged to extend from opposed sides, such as lateral and medial sides, of the adjustment device 30. These segments transversely extend across the width of the foot cosmesis and are aided by guide members 24 along either the interior or exterior side of its dorsal section 12.

The adjustment device may be secured to other components of the foot prosthesis, either permanently or removably. Alternatively, the adjustment device can be removably attached to the cosmesis.

As illustrated in FIG. 2, the guide members 24 are attached to the inner surface 26 of the cosmesis 10 to both guide and retain the elongate element 32. The elongate element may be a cable, lace or other suitable elongate element that can be regulated in length extending from the adjustment device. The guide members 24 are configured to engage the elongate element and may preferably define an open channel or hook having, for example, a semi-circular cross section. The guide members 24 also cooperate with each other to define a path for the elongate element 30.

The guide members 24 may be adhesively bonded, molded or otherwise constructed to provide channels or other suitable structure for cooperating with the elongate element and the cosmesis. The guide members may be located within the cosmesis to provide a more realistic appearance, but may be provided along the exterior of the cosmesis as considered necessary. In this embodiment, an outlet 52 is provided through the thickness 36 of the cosmesis 10 through which the elongate element 32 extends to the adjustment device 30.

The guide members may be arranged in a network of guide members 24 arranged at localized areas of the cosmesis in a pattern 54. For example, the guide members may be located between the heel and toe portions 16, 17 along only the upper or dorsal portion 12 of the cosmesis 10. In this arrangement, the dorsal portion 12 is arranged to collapse upon tensioning of the at least one elongate element, whereas the lower or plantar portion 14 is generally maintained in the predetermined shape configuration.

In the depicted embodiment of FIGS. 1-4, the elongate element 32 has first and second ends (not shown) engaging the adjustment device 30. The elongate element 32 pulls at an anchor guide 56 forming part of the network of guide members 24. Additional anchor guides 56 may be provided along the length of the network of guide members 24 according to the pattern 54.

Figure 4:
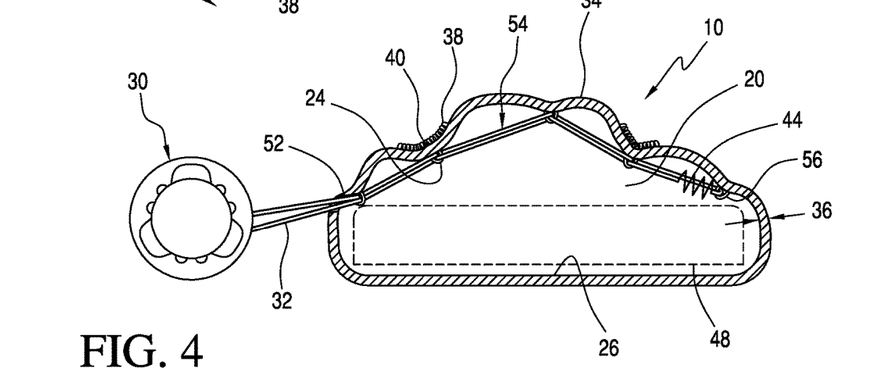
FIG. 4 is a cross-sectional view of the foot cosmesis of FIG. 3 along the line B-B.

While the path of the elongate element is shown in FIGS. 2 and 4 to be generally in a symmetrical configuration extending across the lateral and medial sides of the cosmesis, it should be appreciated that segments of the elongate element may be arranged in different paths relative to one another in variations of the cosmesis. The guide members 24 may be formed integrally with the foot cosmesis and are arranged to define a lace path stretching across a width of the foot cosmesis. The guide members define a lace path that moves in a direction transverse from the length of the cosmesis.

The at least one elongate element may be provided within the thickness 36 of the cosmesis and extend through a plurality of channels formed within the thickness 36. Alternatively, the at least one elongate element may extend through channels located on one of the inner or outer surfaces 26, 34 of the cosmesis 10, in a similar manner discussed in relation to FIGS. 6 and 7.

The adjustment device may be dial tensioning device provided by BOA Technology Inc., or an adjustment device described in U.S. Pat. No. 7,198,610, granted Apr. 7, 2007, and U.S. patent application publication no. 2009/0287128, published Nov. 19, 2009, which are incorporated herein by reference. Alternatively, the adjustment device may be a linear ratchet as taught in U.S. patent application publication no. 2006/0135900, published Jun. 22, 2006, and incorporated herein by reference. Other adjustment devices known to one having ordinary skill in the art may be used that provide locking unidirectional tensioning and release of an elongate element.

The adjustment device 30 may include a housing and a circular knob rotatably mounted thereto. The knob may be rotatable to wind an end of the elongate element 32 into the housing, providing tension to the elongate element. This tension reduces the slack in the elongate element 32 and correspondingly increases the desired level of tightness applied to the cosmesis 10. It should be appreciated that the adjustment device 30 may alternatively be operated to decrease the tension applied to the elongate member to increase its amount of slack, and correspondingly decrease the level of tightness applied to the cosmesis.

The adjustment device may attach to the inside of the foot cosmesis, either directly or to a mount on either side of the cover. A guide rack on or inside the top of the cosmesis may be necessary to enable the cosmesis to fold correctly when the adjustment device is used to tension the elongate element. The elongate element may extend transversely across the width of the foot cover, longitudinally, and/or at various angles along the foot cover.

As previously described, the foot cosmesis 10 is preferably constructed of a flexible material to allow for the cosmesis to be flexed similar to a natural foot. The cosmesis may be constructed from polyurethane foam, although other forms are considered such as polyurethane solid and EVA foam, or other elastomeric materials. The resiliency of the material allows the interior cavity 20 of the cosmesis to transform from an expanded state to a collapsed state, and back to its original expanded state.

Figure 3:
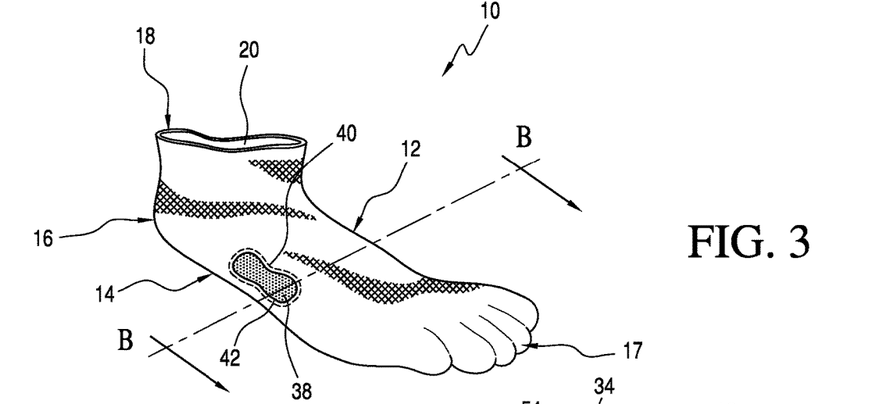
FIG. 3 is a perspective view of the foot cosmesis of FIG. 1 in a collapsed or contracted configuration.

Specifically, using the adjustment device 30 to tighten the elongate element 32 results in an increase in tension applied to the elongate element across a width of the dorsal region 12. This tension causes the dorsal region 12 to collapse, thus altering the shape of the cosmesis as illustrated in FIGS. 3 and 4. As the dorsal region 12 collapses in the direction toward the plantar surface 14, the internal volume of the inner cavity 20 of the cosmesis correspondingly decreases. The resulting shape of the cosmesis is noticeably narrower and may provide for improved tightening against or about a prosthetic foot. The elongate element may cinch a top portion or dorsal region of the cover, and the bottom portion or plantar region, although regarding the plantar region; the prosthetic foot may constrain movement of the cover.

Various reinforcement patches or zones may be used or incorporated into the cover to improve wear resistance.

Variable material thickness and reinforcements may be employed for correctly folding the foot cover and cosmesis as a whole.

Decreasing the volume of the interior cavity 20, and shrinking the size of the cosmesis, makes insertion of the cosmesis into footwear easier since it reduces or eliminates frictional contact between the footwear and the cosmesis. This also helps prevent the cosmesis from sustaining unnecessary wear and tear, especially at high stress contact points.

Upon properly fitting the collapsed cosmesis inside the footwear, the adjustment device 30 can relieve the tension applied to the elongate element 32. By providing enough slack to the elongate element, the resiliency of the cosmesis material allows the volume within the interior cavity 20 to increase expanding the cosmesis back to its original non-collapsed state. Increasing the size of the cosmesis while it is inserted inside the footwear causes the corresponding expansion of the inner cavity to create a proper fit with the footwear. It should be appreciated that to provide the user with sufficient walking stability, the fully expanded cosmesis is preferably sized to properly fit within most footwear such that free play between the cosmesis and the footwear is minimal.

Since the adjustment device 30 both tightens and loosens the elongate element 32, it may further assist tightening/loosening the cosmesis directly to the prosthetic foot. This provides an easy way for a user to tighten the cosmesis if it becomes loose while wearing it during a day. As previously described, such quick and easy adjustment to the fit of the cosmesis on a prosthetic device can advantageously be accomplished quickly. Improved tightening of the cosmesis over a prosthetic foot shields it from contact with dirt and other debris. Sufficiently securing the cosmesis to an artificial foot helps reduce or eliminate the repeated frictional contact between the artificial foot and the cosmesis.

Referring to FIG. 4, an outer surface 34 of the cover 10 opposed to an inner surface 26 of the cover 10 may include a surface roughness 38. The surface roughness 38 may be imparted onto the cover 10 by incorporation of abrasive materials into the material forming the cover or applied to the cover by at least one supplementary material in a patch, strip or other suitable material 42. The surface roughness 38 may cover the entire cover or be provided in patterns or discrete areas 38.

An exemplary surface roughness 38 may be a tacky and high friction area achieved by a film, layer or discrete friction materials. Alternatively, the surface roughness can be a hook and loop type material that can engage with itself when folded or rubbed against opposed surfaces.

FIG. 4 shows the surface roughness 38 as being located within areas 40 where the cover 10 will fold. The fold areas 40 gain traction with opposing surfaces to keep the cover 10 movement upon insertion into a shoe so it can slip into a shoe without or minimal friction.

Figure 5:
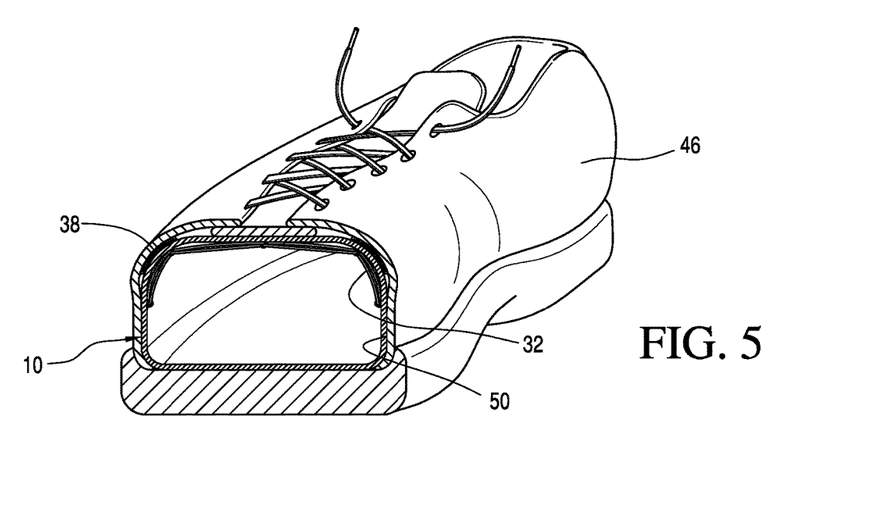
FIG. 5 is a schematic view of the foot cosmesis of FIG. 1 in a shoe.

The surface roughness 38 is provided at least along the outer surface 34 so that where the cover folds when the adjustment device 30 tightens the elongate element 32, the cover 10 can be slid easily into a shoe with folded portions 40 of the cover 10 holding to one another without slippage. When the elongate element 32 is released, the surface roughness 38 provides high friction areas arranged for gripping the interior surface 50 of a shoe 46, as shown in FIG. 5. The surface roughness 38 forms a suspension mechanism both allowing the cover 10 to slide easily into a shoe when the cover 10 is in a closed or contracted configuration (as in FIG. 2) while providing means for retaining the shoe on the cover 10 when the cover 10 is in the expanded, normal or relaxed configuration (as in FIG. 4).

The expanded configuration of the cosmesis 10, as in FIGS. 1 and 2, may be a predetermined shape of the cosmesis, such that the cosmesis is formed in such shape, and will be considered the shape of the cosmesis even if it is temporarily deformed, collapsed or compressed, as in FIGS. 3 and 4. The material forming the cosmesis 10 may be both flexible and resilient, such that the resiliency of the material will urge the cosmesis 10 into the predetermined shape after any force urged on the cosmesis is released, whether it is from the adjustment device by releasing tension in the elongate element or after the cosmesis is slid into a shoe and expands into the cavity of the shoe. From the foregoing, the resiliency of the cosmesis 10 allows the cosmesis to bounce to its predetermined shape.

The return to the predetermined shape may be facilitated by adding a spring 44, as in FIG. 4, to the elongate element to enable more tensioning and release of the elongate element due to tightening and release of the adjustment device between the expanded or predetermined shape, and the collapsed or compressed condition. The cosmesis may include other elements such as bars, plates, reinforcements for increasing the resiliency or resistance between the expanded and collapsed conditions. Alternatively, the wall thickness 36 can be modified to increase or decrease resiliency of the cosmesis.

Figures 6, 7:
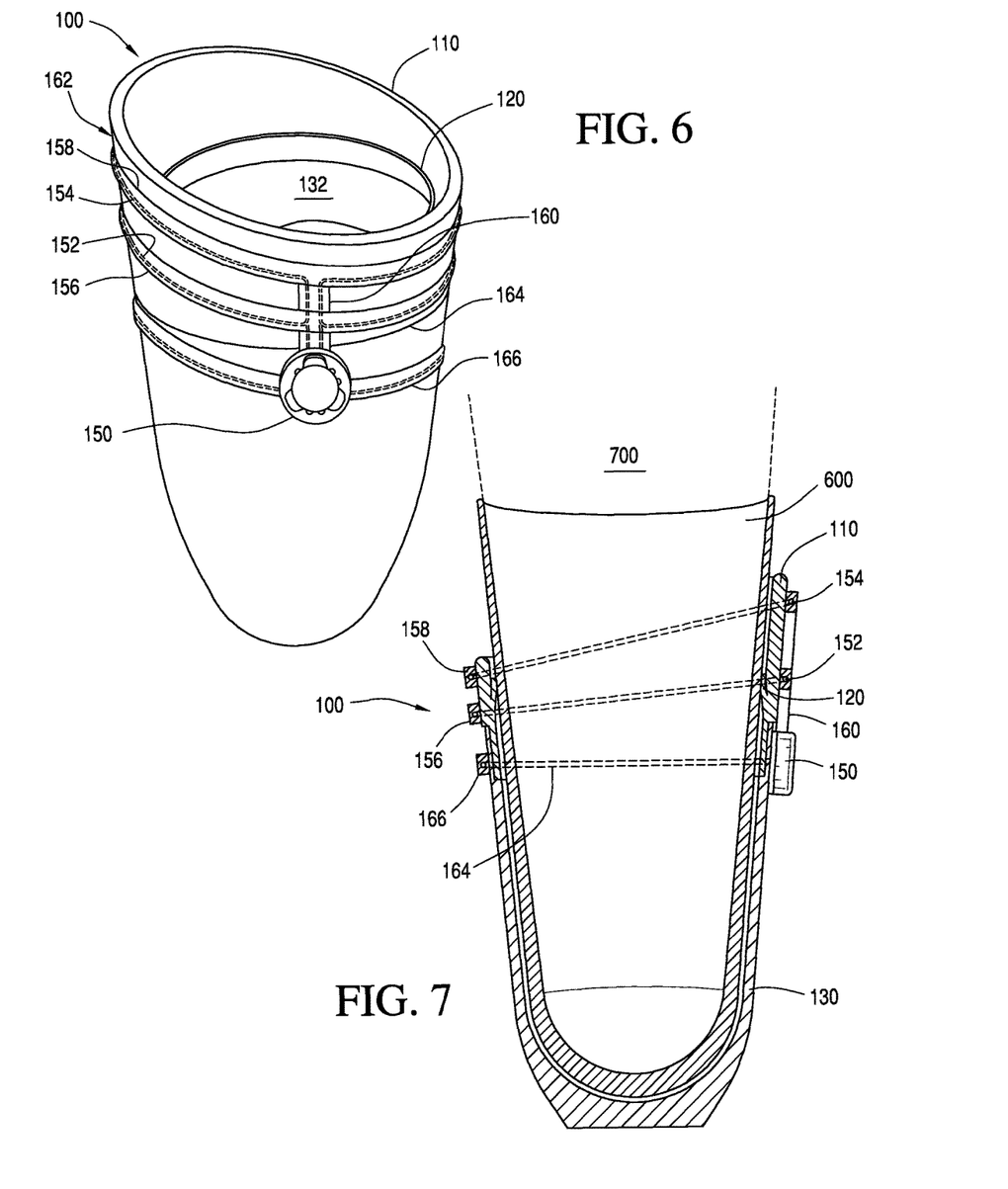
FIG. 6 shows a front view of an embodiment of a socket and attached brim attachment in a closed or contracted configuration.
FIG. 7 is a cross-sectional view of the embodiment of FIG. 6 in combination with a prosthetic liner.

FIGS. 6 and 7 depict another adjustable prosthetic device in a socket 130 with a brim attachment 100 generally forming a resilient body and an adjustment device 150. The socket 130 with the brim attachment 100 may be arranged as in U.S. patent application publication 2015/0051711, published Feb. 19, 2015 and incorporated herein by reference.

An example of a socket, as is readily understood by the skilled artisan in prosthetics, is described in U.S. Pat. No. 7,438,843, granted Oct. 21, 2008, the entirety of which is incorporated herein by reference. The liner may be formed under any of the following U.S. Pat. No. 6,136,039, granted Oct. 24, 2000, U.S. Pat. No. 6,626,952, granted Sep. 30, 2003, and U.S. Pat. No. 7,118,602, granted Oct. 10, 2006, each of which is incorporated by reference in its entirety. The liner may create a seal between the socket and the liner, as disclosed in U.S. Pat. No. 8,097,043, granted Jan. 17, 2012 and incorporated by reference in its entirety.

FIG. 6 shows the brim attachment 100 as including a cuff section 110 and a seal element 120. The cuff section 110 and seal element 120 are sufficiently elastic and resilient to allow the cuff section 110 and seal element 120 to return to relaxed positions after they are bent and/or stretched. The brim attachment 100 and the cuff section 110 can be ergonomically formed so the brim attachment 100 comfortably fits over a residual limb whether or not donning a liner when inserted into the socket 130.

The adjustment device 150 secures to the socket 130 and includes at least one elongate element wherein the example shows two elongate elements 152, 154 coupled to the adjustment device 150 and extending about the cuff section 110. The elongate elements 152, 154 may be routed through guides or channels 156, 158 either formed by the cuff section 110 in which the channels are molded in the thickness of the cuff section 110, or formed along a surface of the cuff section 110 by material of the cuff section 110, as depicted in FIG. 6.

Channels 156, 158 may be separate from the cuff section 110 and secured along an outer or inner surface of the cuff section 110. A guide 160 may direct the elongate elements 152, 154 to the adjustment device 150. The guide and channels may be continuous in that they extend generally circumferentially about the brim attachment and socket, or alternatively may be comprised of a plurality of segments through which the elongate element extends.

Each channel may be arranged to permit sliding of the at least one elongate element and it is preferred there is sufficient material of the cuff section to enable circumferential tensioning by the elongate element. It is also preferable that the channel evenly distributes pressure to avoid pressure points brought by the elongate element over the liner. When in a relaxed position, the seal element 120 functions as a seal around a liner 600 inserted into the socket 130, and may be improved by the location of the channel relative to the seal.

FIG. 7 depicts the elongate element 156 as being generally concentric and generally at the same height with at least a portion of the seal element 120. The same height indicates that the elongate element and corresponding channel, if provided, is generally at a same or within an axial segment formed by the seal element 120. This arrangement enables better sealing of the seal element 120 against an outer surface of the liner (the surface adjacent an inner surface of the socket) since the elongate element circumferentially tensions about the seal element 120 and controllably presses the seal element against the liner.

The embodiment of FIG. 6 is not limited to two elongate elements 152, 154, and may be modified to include a single elongate element or more than two elongate elements. The elongate elements should be arranged on the cuff section to distribute circumferential tensioning of the elongate elements to securely hold or maintain the shape of the brim attachment 100 to seal against a prosthetic liner, as discussed in U.S. patent application publication 2015/0051711 and shown in FIG. 7.

The adjustment device 150 may be secured to the socket 130 or to the cuff section 110, although FIGS. 6 and 7 depict the adjustment device 150 being secured to the socket 130. The adjustment device 150 may be permanently or releasably mounted onto the socket 130 or brim attachment 100.

At least one channel or other suitable means may be provided along at least a side of the socket where the brim has a minimum height for providing additional support and counterforce from the hard socket structure relative to the brim structure which is substantially flexible and resilient. As shown in FIGS. 6 and 7, the elongate element 152, 154 extends over the invertable part 162 of the cuff section 110, as taught in U.S. patent application publication 2015/0051711. An additional channel 166 is located on the socket 164 proximate to a distal portion of the brim attachment 100, and engages the attachment device 150. The channel 166 may circumferentially extend about the socket 130 or may only be provided along a segment of the socket 100 tailored to provide a discrete area of counterforce.

FIG. 6 shows the cuff 110 and seal element 120 in a relaxed position, whereas the adjustment device 150 is arranged for tensioning the elongate elements 152, 154. The cuff section 110 and seal element 120 are generally not under tension, and are positioned in their respective natural states. In the relaxed position, the cuff section 110 extends upwards from the socket 130, and the seal element 120 extends inwardly towards the middle of the opening of the socket 130.

FIG. 7 shows a liner 600 in combination with the flexible brim 110 substantially parallel to both the socket 130 and a residual limb 700 inserted into the liner 600 and socket 130. The seal element 120 is positioned in a sealing configuration such that the seal element 120 functions as a seal between the cuff section 110 and a liner 600 and may be controllably pressed against the liner 600 by the adjustment device 150 via the at least one elongate element 152, 154.

Once a seal has been established a vacuum can be created between the inner walls of the socket 130 and the liner 600. One will understand that creating a vacuum within the socket 130 can provide a wearer of the prosthetic limb with improved proprioception and volume control. In view of the above disclosure, one will understand that the brim attachment can also easily release a vacuum created by the seal element 120. A vacuum can be released by pulling the cuff section 110 outward or otherwise reflecting the cuff section 110. Once the cuff section 110 is reflected such that the adjustment device 150 and the at least one elongate element 152, 154 is detensioned, the vacuum can be released and a liner 600 and residual limb can easily be removed from the socket 130.

The brim attachment of FIGS. 6 and 7 may be extended to a liner such that the brim attachment is incorporated into the liner, either by molding or attachment, and an adjustment device is secured to the liner in combination with the channels to urge the brim attachment and corresponding seal to the skin or against the residuum of an amputee.

Although the embodiments have been disclosed in certain exemplary embodiments and examples, it therefore will be understood by those skilled in the art that the present invention extends beyond the specifically disclosed embodiments to other alternative embodiments and/or uses of the invention and obvious modifications and equivalents thereof. It is intended that the present invention disclosed should not be limited by the particular disclosed embodiments described above.

What is claimed is:

1. A lower leg prosthesis system, comprising:
   a prosthetic foot;
   a foot cosmesis including a resilient body formed from an elastomeric material and having a predetermined shape configuration, the resilient body having an inner surface and an outer surface opposed to the inner surface and separated by a wall thickness, the resilient body defining a cavity delimited by the inner surface of the resilient body,
   an adjustment device connected to the resilient body,
   a network of guides attached along the inner surface and contained within the cavity; and at least one elongate element having a first end received by the adjustment device such that the adjustment device is arranged to regulate tension in the at least one elongate element,
   the at least one elongate element having a second end anchored to the least one guide of the network of guides, the at least one elongate element extending between and through the guides within the cavity;
   wherein tensioning of the at least one elongate element by the adjustment device urges the resilient body to collapse or compress into a contracted configuration;
   wherein compression of the resilient body is achieved by tensioning of the at least one elongate element and pulling the resilient body from within the cavity via the guides located therewithin into compression from the inner surface thereof, wherein release of tension of the at least one elongate element allows the resilient body to revert to the predetermined shape configuration due to resiliency of the elastomeric material of the resilient body when the at least one elongate element is not tensioned;
   wherein the outer surface of the resilient bob has an abrasive material in discrete areas opposite the guides.

2. The lower leg prosthesis system of claim 1, wherein the resilient body defines dorsal and plantar portions, the prosthetic foot arranged for placement in the plantar portion, the at least one guide located in the dorsal portion such that the contracted configuration of the resilient body results in collapsing of the dorsal portion over the plantar portion and the prosthetic foot.

3. The prosthetic device of claim 1, wherein the resilient body defines an outlet provided through a thickness of the resilient body defined between the inner and outer surfaces, a length of the at least one elongate element extending between the second end of the at least one elongate element and the outlet extending through at least two of the at least one guide of the network of guides.

* * * * *